US007105327B1

(12) United States Patent
Kuppusamy et al.

(10) Patent No.: US 7,105,327 B1
(45) Date of Patent: Sep. 12, 2006

(54) RECOMBINANT STREPTOKINASE

(75) Inventors: Mosuvan Kuppusamy, Secunderabad (IN); Vellimedu Kannappa Srinivas, Secunderabad (IN); Subhra Lahiri, Hyderabad (IN); Krishna Ella, Hyderabad (IN); Ghan Shyam Khatri, Hyderabad (IN)

(73) Assignee: Bharat Biotech International, Ltd., (IN)

( * ) Notice: Subject to any disclaimer, the term of this patent is extended or adjusted under 35 U.S.C. 154(b) by 600 days.

(21) Appl. No.: 09/882,509

(22) Filed: Jun. 15, 2001

(51) Int. Cl.
*C12N 1/20* (2006.01)
*C12N 9/12* (2006.01)
*C12N 15/12* (2006.01)
*C07H 21/04* (2006.01)

(52) U.S. Cl. ............... 435/194; 435/320.1; 435/252.3; 435/252.33; 536/23.2

(58) Field of Classification Search ............ 435/320.1, 435/194, 252.3, 6, 252.33; 536/23.2
See application file for complete search history.

(56) References Cited

U.S. PATENT DOCUMENTS

| 2,701,227 A |   | 2/1955  | Ablondi et al. |
|-------------|---|---------|-----------------------|
| 3,855,065 A |   | 12/1974 | Feldman |
| 5,011,686 A | * | 4/1991  | Pang ............... 424/94.1 |
| 5,296,366 A |   | 3/1994  | Garcia et al. |
| 5,708,148 A | * | 1/1998  | Schmitz et al. ....... 530/402 |

OTHER PUBLICATIONS

Pupo et al., Biotechnology Letters, 21, 1119-1123, 1999.*
Amery, A., and Claeys, H. (1970), *Hemat Rev.*, 2:233.
Badimon, L. and Badimon, J.J. (1989), *J. Clin. Invest.*, 84:1134-1144.
Bernheimer, J. et al. (1942), *J. Bact.*, 43:481-494.
Chesebro, J.H., Knatterud, G., Roberts, R., et al. (1987), *Circulation*, 76:142-154.
Costellino, F.J., Sodetz, J.M., Brockway, W.J., Seifring, G.E. Jr. (1977), *Methods in Enzymology*, XLV:244-257.
Granger, C.B., Califf, R.M., Jopol, E.J. (1992), *Drugs*, 44(3):293-325.
Jorgensen, L., Rowsell, H.C., Hovig, T., Mustard, J.F. (1967). *Ann. J. Pathol*, 51:681-719.
Malke, et.al. (1985), *Gene*, 34:357-362.
Marston, F.A.O., Lowe, P.A., Doel, M.T. et al. (1984), *Bio/technology*, 2:800-804.
McClintock, D.K, and Bell, P.H. (1971), *Biochem. Biophys. Res. Commun*, 43:694-702.
Miller, G., (1959) *Anal. Chem.* 31:426-428.
Radcliffe, R. and Heinze, T. (1981), *Arch. Biochem. Biophys.* 211(2):750-761.
Robbins, K.C., Summaria, L. (1976), *Methods in Enzymology.* 45:257-273.
Sambrook, J., Fritsch, E.F., and Maniatis, T., *Molecular Cloning: A Lab Manual.* 2nd edition. Cold Spring Harbor Laboratory Press, Cold Spring Harbor, New York (1989) (copy not provided).
Topal, E.J., Thrombolytic Intervention. In Topal, E.J.(Ed). Textbook of Interventional Cardiology. pp. 76-120. W.B. Saunders Co., Philadelphia, 1991 (Copy not provided).
Verstraete, M., Bory, M., Collen, D. et.al. (1985). *Lancet* 1:842-847.

* cited by examiner

Primary Examiner—Maryam Monshipouri
(74) Attorney, Agent, or Firm—Joseph T. Leone, Esq.; DeWitt Ross & Stevens S.C.

(57) ABSTRACT

The present invention is based on the isolation of a gene coding for streptokinase from *Streptococcus equisimilis* (ATCC 9542), its cloning, and expression in *E. coli*. Two different strategies were carried out for the production of enzymatically-active streptokinase. In the first strategy, streptokinase was expressed as an inclusion body without its signal sequence followed by purification, solubulization, and renaturation to obtain an active preparation. The purified enzyme was formulated and lyophilized. In the second strategy, enzymatically-active streptokinase is secreted into the culture medium. The enzyme was purified, formulated and lyophilized.

8 Claims, 14 Drawing Sheets

Lane A: Uninduced
Lane B: Uninduced
Lane C: Ovalbumin (45 Kd)
Lane D: Induced
Lane E: Induced Lane A: After fermentation
Lane B: Ovalbumin
Lane C: Formulated Lane A: Aqueous phase after PEG precipitation
Lane B: Standard marker (45 Kd)

Lane A: Fraction of Ion exchange column
Lane B: Fraction of Gel permeation column Lane A: Purified Streptokinase (45 Kd)
Lane B: Formulated Streptokinase (with human serum albumin)

SEQUENCE LISTING

```
<160> NUMBER OF SEQ ID NOS: 5

<210> SEQ ID NO 1
<211> LENGTH: 24
<212> TYPE: DNA
<213> ORGANISM: Artificial Sequence
<220> FEATURE:
<223> OTHER INFORMATION: Synthetic PCR primer

<400> SEQUENCE: 1
ggaattcatg aaaaattact tatc                                              24

<210> SEQ ID NO 2
<211> LENGTH: 26
<212> TYPE: DNA
<213> ORGANISM: Artificial Sequence
<220> FEATURE:
<223> OTHER INFORMATION: Synthetic PCR primer

<400> SEQUENCE: 2
ggatccttat ttgtcgttag ggttat                                            26

<210> SEQ ID NO 3
<211> LENGTH: 1245
<212> TYPE: DNA
<213> ORGANISM: Streptococcus equisimilis (ATCC 9542)

<400> SEQUENCE: 3
attgctggac ctgagtggct gctagaccgt ccatctgtca acaacagcca attagttgtt        60
agcgttgctg gtactgttga ggggacgaat caagacatta gtcttaaatt ttttgaaatt       120
gacctaacat cacgacctgc tcatggagga aagacagagc aaggcttaag tccaaaatca       180
aaaccatttg ctactgatag tggcgcgatg ccacataaac ttgaaaaagc tgacttacta       240
aaggctattc aagaacaatt gatcgctaac gtccacagta acgacgacta ctttgaggtc       300
```

-continued

```
attgattttg caagcgatgc aaccattact gatcgaaacg gcaaggtcta ctttgctgac    360
aaagatggtt cggtaacctt gccgacccaa cctgtccaag aattttttgct aagcggacat    420 gtgcgcgtta gaccatataa agaaaaacca atacaaaatc aagcgaaatc tgttgatgtg    480
gaatatactg tacagtttac tcccttaaac cctgatgacg atttcagacc aggtctcaaa    540
gatactaagc tattgaaaac actagctatc ggtgacacca tcacatctca agaattacta    600
gctcaagcac aaagcatttt aaacaaaacc cacccaggct atacgattta tgaacgtgac    660
tcctcaatcg tcactcatga caatgacatt ttccgtacga ttttaccaat ggatcaagag    720
tttacttacc atgtcaaaaa tcgggaacaa gcttatgaga tcaataaaaa atctggtctg    780
aatgaagaaa taaacaacac tgacctgatc tctgagaaat attacgtcct taaaaagggg    840
gaaaagccgt atgatccctt tgatcgcagt cacttgaaac tgttcaccat caaatacgtt    900
gatgtcaaca ccaacgaatt gctaaaaagc gagcagctct taacagctag cgaacgtaac    960
ttagacttca gagatttata cgatcctcgt gataaggcta aactactcta caacaatctc   1020
gatgcttttg gtattatgga ctataccta actggaaaag tagaggataa tcacgatgac   1080
accaaccgta tcataaccgt ttatatgggc aagcgacccg aaggagagaa tgctagctat   1140
catttagcct atgataaaga tcgttatacc gaagaagaac gagaagttta cagctacctg   1200
cgttatacag ggacacctat acctgataac cctaacgaca aataa                    1245
```

<210> SEQ ID NO 4
<211> LENGTH: 12
<212> TYPE: PRT
<213> ORGANISM: Streptococcus equisimilis (ATCC 9542)

<400> SEQUENCE: 4

Ile Ala Gly Pro Glu Trp Leu Leu Asp Arg Pro Ser
1               5                   10

<210> SEQ ID NO 5
<211> LENGTH: 5
<212> TYPE: PRT
<213> ORGANISM: Streptococcus equisimilis (ATCC 9542)

<400> SEQUENCE: 5

Lys Asp Asp Pro Asn
1               5

RECOMBINANT STREPTOKINASE

FIELD OF THE INVENTION

The present invention relates to thrombolytics. In particular, the invention is directed to recombinant streptokinase (SK) which can be used in the treatment of heart diseases such as myocardial infarction.

BIBLIOGRAPHY

Complete bibliographic citations to the references noted herein are included in the Bibliography immediately preceding the claims.

BACKGROUND OF THE INVENTION

Thromboemolism, a significant medical problem, is manifested by the occlusion of blood vessels due to the presence of blood clots (thrombi) (1). Thrombi are composed of fibrin and blood cells and may form in any part of the cardiovascular system including the veins, arteries, heart and microcirculation (2). As thrombi age, they undergo progressive structural changes; leucocytes are attracted by chemotactic factors released from the aggregated platelets or proteolytic fragments of plasma proteins and become incorporated into the thrombi (3). These aggregated platelets swell and disintegrate and are gradually replaced by fibrin (4). Such clots often affect organs such as the heart and lungs. These clots may loosen and circulate to smaller arteries.

Timely restoration of blood flow through the damaged blood vessels is an important curative goal of medical practices (5). Normal blood flow can be restored by the use of fibrinolytic agents. These agents are called thrombolytic agents, and include streptokinase, other thrombolytic agents, such as urokinase and tissue plasminogen activators are also used in the treatment of myocardial infarction, pulmonary, arterial or venous thromboembolism, surgical adhesions and other cases (6–8,13).

Thrombolytic agents facilitate the in vivo lysis or dissolution of the clot (9). They act by converting endogenous plasminogen (a proenzyme) to plasmin (an active enzyme), which lysis the clot (10–11).

Plaminogen is a single chain glycoprotein, which in its native form has an amino-terminal glutamic acid. It is converted to plasmin by the cleavage of an Arg-Val (560–561) peptide bond (12).

Streptokinase is a single chain polypeptide that binds to plasminogen in a 1:1 ratio. This causes conformational changes so that the complex becomes an active enzyme. This complex cleaves peptide bonds on other plasminogen molecules to produce more plasmin (14).

Bernheimer et al. (1942) (15) have elucidated in detail the media requirements for growth of streptococci. U.S. Pat. No. 2,701,277 describes two primary nitrogenous materials employed in the fementative production of streptokinase by hemolytic streptococci in which the expression of streptokinase is very low (16).

U.S. Pat. No. 3,855,065 describes an improved production process by employing corn steep liquor in the culture medium. However, when streptokinase is prepared from streptococcal cultures grown under these conditions, complex downstream processing is required to remove pyrogenic material such as gram negative bacteria, streptolysin, and other secretory proteins (17).

Streptokinase from Group C streptococci has been purified for clinical usage and studied by several investigators. The primary source of SK has been the culture fluid resulting from the growth of the beta-hemolytic Group C Lansfield *streptococcus* from a gram negative strain containing other secretory substances which are toxic and pyrogenic to mammals. Extensive purification of the enzyme has become mandatory for its use as a treatment to dissolve thrombi.

Advances in biotechnology have made it possible to excise the streptokinase gene (SK gene) and introduce the gene into other prokaryotic organisms, and thus express the recombinant protein. The host organism, referred to as a recombinant organism, not only has the ability to express the foreign gene, but can also grow to high cell density during fermentation.

German Patent publication IPC C12 N 15/00 describes the cloning and expression of the SK gene from *Streptococcus equisimilis* strain H46A (ATCC 12449) in an *E. coli* host and reports a low yield of 0.1 to 1.8 mg/liter (18). Malke et al. (1985) report the nucleotide sequence of native streptokinase from *Streptococcus equisimilis* H46A (19) (ATCC 12449). U.S. Pat. No. 5,296,366 describes the isolation and cloning of the streptokinase gene under the trp promoter and expressed in *E. coli*. The transformants produced 350 mg of streptokinase/Liter of medium (20).

SUMMARY OF THE INVENTION

The present invention relates to improved recombinant streptokinase derived from *Streptococcus equisimilis* (ATCC 9542) which can be used in the treatment of heart diseases, especially myocardial infarction. The initiating event of many myocardial infarctions is a hemorrhage in atherosclerotic plaque, which ultimately leads to the formation of thrombi (blood clots) in the coronary arteries. Thrombi are mainly composed of a combination of fibrin and blood platelets. The formation of a thrombi has very serious clinical ramifications.

The primary goal of a successful therapy is not only to dissolve the clot but also to prevent its reformation after the cessation of the therapy. The dissolution of the clot can be achieved through the use of thrombolytic agents. Such agents include streptokinase, urokinase, and tissue plasminogen activator.

In the present invention, two processes are described for the production of highly purified, recombinant SK. In the first strategy, SK gene was cloned in plasmid vector without its signal sequence (BBIL-SK) and was expressed as a cytoplasmic inclusion body. The expression of SK was brought about using λpR-λpL promoter. The inclusion body was then purified by various techniques such as solubulization, renaturation and chromatography. The pure SK was then characterized, formulated and lyophilized.

In the second strategy, a two-plasmid system was used to secrete SK into the culture media. The SK gene-coding vector used to transform the *E. coli* host also harbors another plasmid which produces Bacteriocin Release Protein (BRP). Induction of this plasmid results in the formation of permeable zones in the cell envelope through which the recombinant streptokinase is secreted into the culture medium. This prevents the accumulation of streptokinase as inclusion body with the cell cytoplasm.

After fermentation of the recombinant host to form the SK, various methods have been used for the purification of the inclusion body, including solublization, renaturation and purification of the recombinant protein to obtain an active, purified enzyme.

The objects and advantages of the invention will appear more fully from the following detailed description of the

BRIEF DESCRIPTION OF THE DRAWINGS

FIG. 1A depicts the fabrication of the streptokinase insert. FIG. 1B depicts the starting pUC18 vector and the cutting of the vector with the restriction enzymes XbaI and BamHI. FIG. 1C depicts the resulting cut in the pUC vector within the multiple cloning site (MCS) of pUC18. FIG. 1D shows the incorporation of the insert of FIG. 1A into the pUC18 vector.

DETAILED DESCRIPTION OF THE INVENTION

Figure 1A:
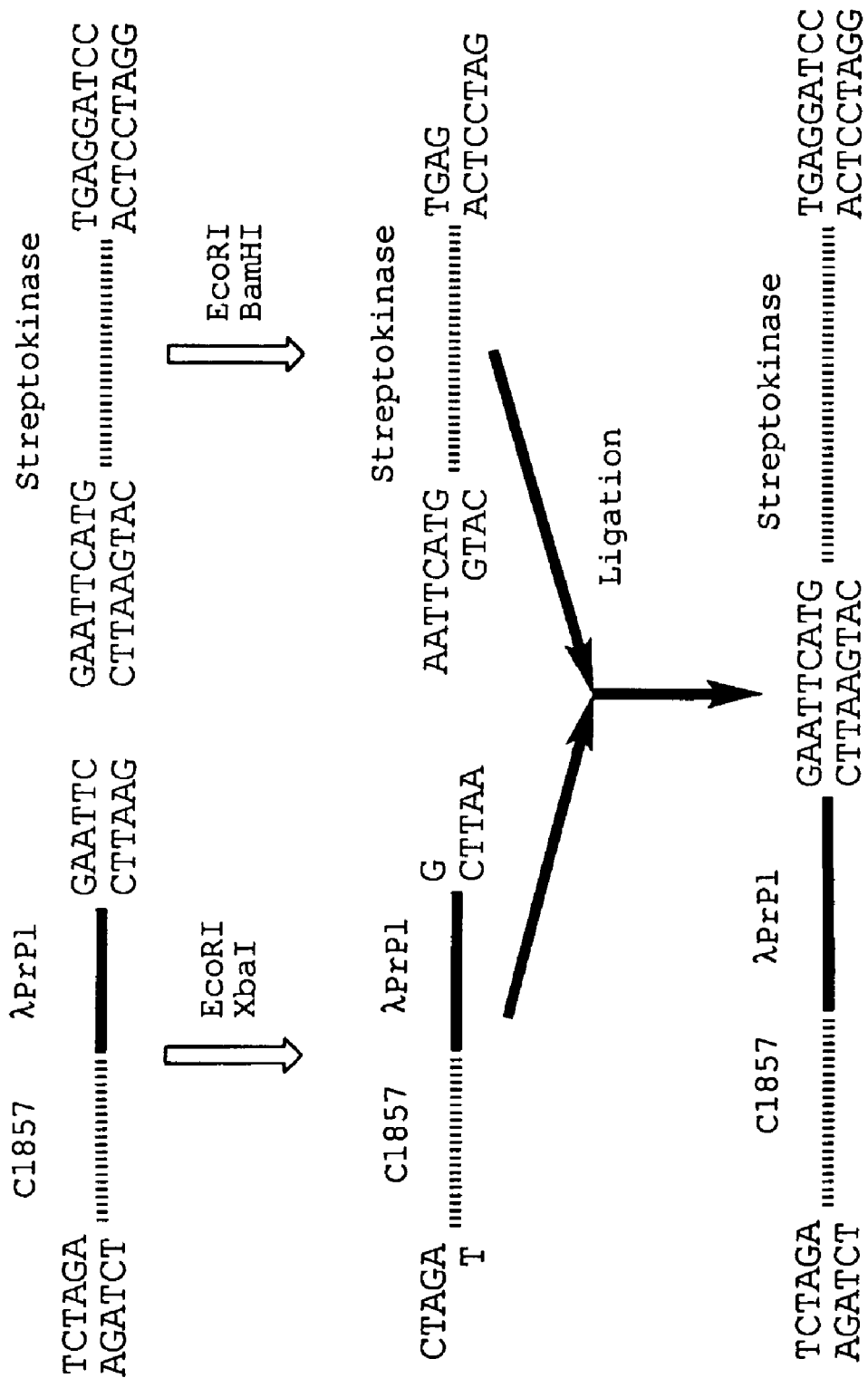
FIGS. 1A, 1B, 1C, and 1D, in combination, depict a schematic representation of the construction of a vector for heat-inducible expression of streptokinase in an *E. coli* host.
Figure 1B:
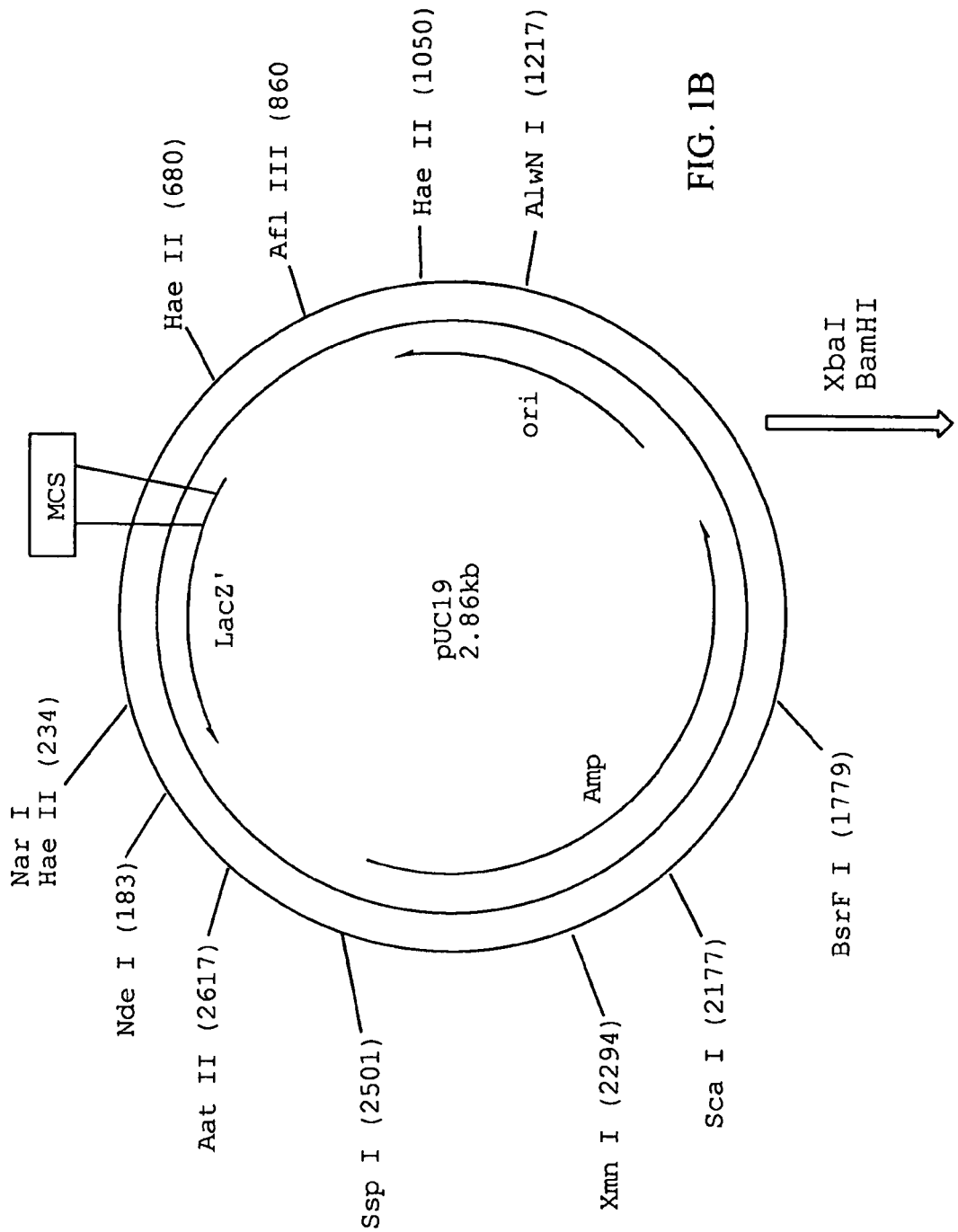
Figure 1C:
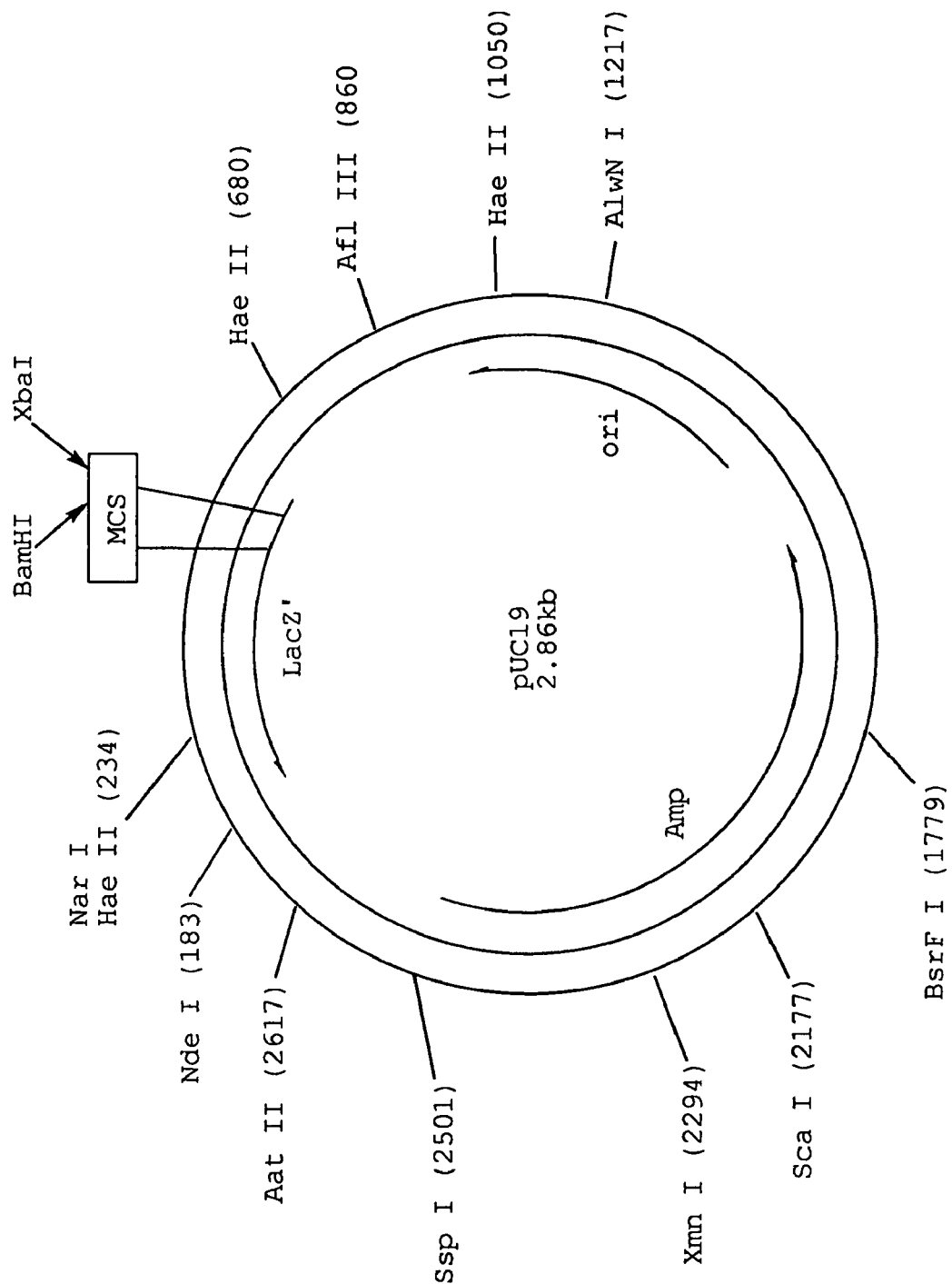
Figure 1D:
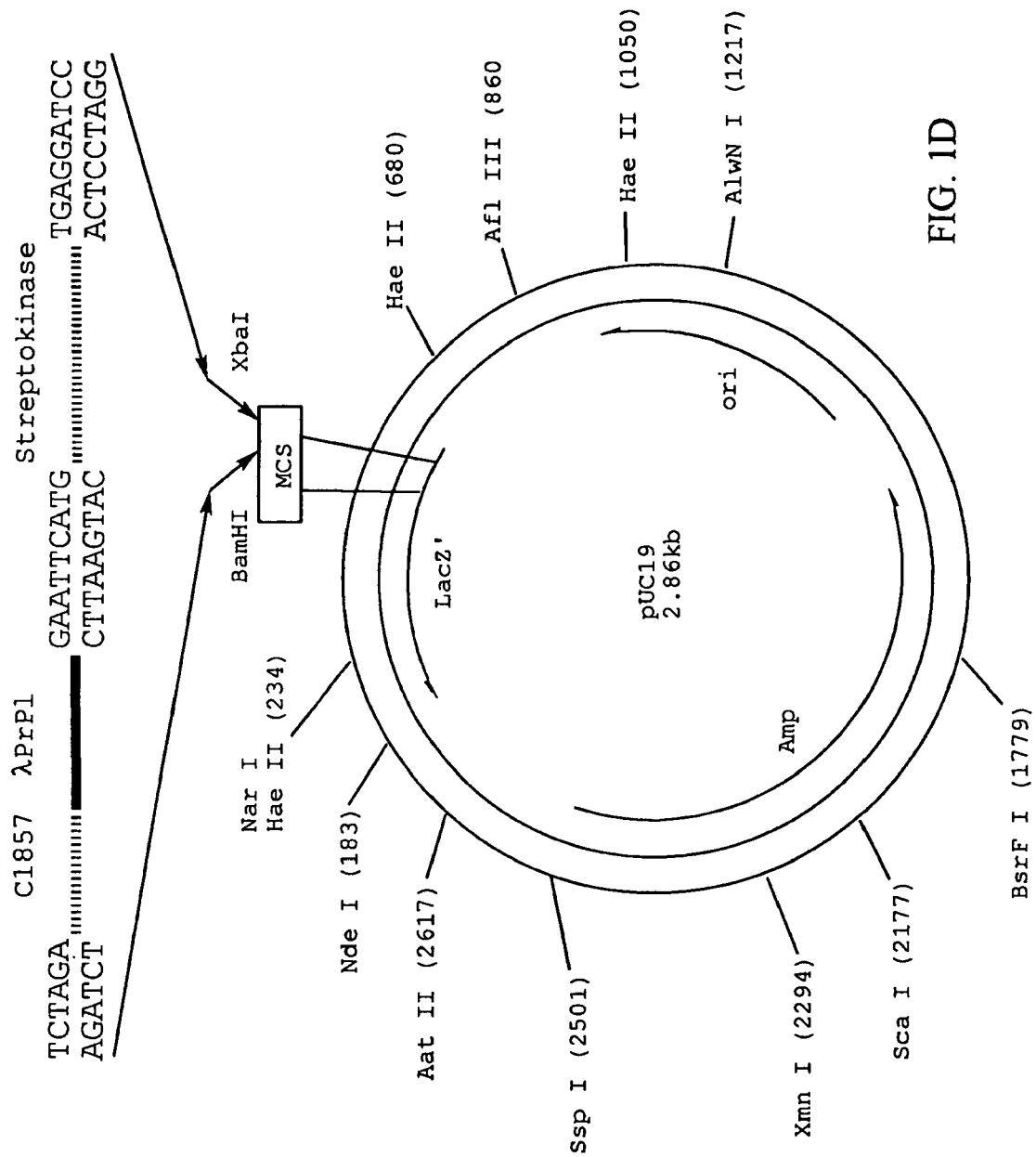

For purposes of the specification and claims, the following definitions are used. All other terms not defined have their standard, accepted meaning in the field of recombinant genetics.

Expression Construct: A DNA construct containing at least one sub-sequence encoding a protein of interest which is operationally linked to one or more regulatory sub-sequences which drive expression of the encoded protein when the construct is transformed into a suitable host cell. Such constructs may also contain sub-sequences encoding means for selecting host cells transformed to contain the construct, such as sub-sequences which confer antibiotic resistance or dietary limitations to transformed cells.

Genetic Engineering: Many of the steps noted below for the manipulation of DNA, including digesting with restriction endonucleases, amplifying by PCR, hybridizing, ligating, separating and isolating by gel electrophoresis, transforming cells with heterologous DNA, selecting successful transformants, and the like, are well known and widely practiced by those skilled in the art and are not extensively elaborated upon herein. Unless otherwise noted, the DNA protocols utilized herein are described in (18).

Host Cells: For industrial applications, the recombinant DNA described herein is incorporated into a host microbe. The host microbe may be any host amenable to transformation, including, but not limited to, microbes of the genera *Saccharomyces, Bacillus, Aspergillus, Pichia, Kluyveromyces, Escherichia* and the like. It is preferred that the host cell be a bacterium. The most preferred host is a strain of *E. coli*.

Operationally Linked: When referring to joined DNA sequences, "operationally linked" denotes that the sequences are in the same reading frame and upstream regulatory sequences will perform as such in relation to downstream structural sequences. DNA sequences which are operationally linked are not necessarily physically linked directly to one another but may be separated by intervening nucleotides which do not interfere with the operational relationship of the linked sequences.

Promoter: The DNA sequence site where RNA polymerase binds to the beginning of an operon. Once bound, the RNA polymerase travels along the DNA in the 5prime to 3prime direction and assembles the corresponding RNA sequences. While the promoter functions as the start signal for RNA synthesis, the promoter itself is not transcribed.

Cloning of Streptokinase Gene: The general approach to the invention is the preparation of an expression vector or cloning vehicle which is capable of replicating and driving the expression of streptokinase in a prokaryotic host, especially in *E. coli*.

Isolation of Genomic DNA: *Streptococcus equisimilis* (ATCC 9542); American Type Culture Collection, 10801 University Blvd., Manassas, Va., 20110, USA) was cultured in 500 ml brain-heart infusion broth (Difco, Franklin Lakes, N.J., USA) at 37° C. The cells were harvested by centrifugation and washed with cold TES buffer (0.03 M Tris, pH 8.0, 0.005 M EDTA and 0.05M NaCl). Cells were resuspended in 15 ml of 25% glucose containing 0.03 M EDTA and subsequently 10 mg of proteolytic enzyme pronase (Sigma Chemical Company, St. Louis, Mo., USA) was added and the cell suspension was incubated at 37° C. for 30 minutes. After incubation, the cells in the mixture were then subjected to further lysis with 20 ml of 1% sodium dodecyl sulphate (SDS) in TES buffer and 5 ml of sodium perchlorate. The cell lysate was extracted with phenol-chloroform solution. The DNA was precipitated with ethanol and washed with 70% cold ethanol and dissolved in TES buffer and purified further by centrifugation by the cesium chloride ethidium bromide method (18). The DNA was subjected to agarose gel electrophoresis, along with known standard markers (Sigma). Purified DNA having an average size of about 50 kb was visualized on staining with ethidium bromide.

Polymerase chain reaction (PCR) of the streptokinase gene: PCR is a technique in which cycles of denaturation, annealing with a primer pair, and extension with DNA polymerase are used to generate a large number of copies of a desired polynucleotide sequence. See U.S. Pat. Nos. 4,683, 195 and 4,683,202 for a description of the reaction.

One µg of the genomic DNA was taken and the gene coding for SKC-2 was amplified by PCR using the following primers:

(SEQ. ID. NO. 1)
5' - GGAATTCATGAAAAATTACTTATC - 3'

(SEQ. ID. NO. 2)
5' - GGATCCTTATTTGTCGTTAGGGTTAT - 3'

For expression as an inclusion body (Strategy I), in each reaction, 100 pmol of each oligonucleotide, 2 units of Taq polymerase (Perkin Elmer, USA) and 200 µmol of each dNTP were used and the reactions were performed in 10 mM $MgCl_2$, 100 mM DTT, and 10 mM NaCl with glycerol. Thirty amplification cycles were performed wherein in each cycle, the reaction was incubated at 95° C. for 1 minute for denaturation, at 52° C. for 45 seconds for hybridization of the oligonucleotides, and at 70° C. for 80 seconds for extension. The nucleotide sequence of the gene is given in SEQ. ID. NO. 3. The gene product thus amplified was digested with EcoRI restriction enzyme.

The vector pUC19 was linearized with EcoRI restriction endonuclease. The reconstructed streptokinase gene was digested with EcoRI restriction endonuclease and inserted into correspondingly digested chimeric expression vector pΔExp to generate the recombinant plasmid BBIL-SK. The schematic construction of the vector (designated BBIL-SK) is given in FIG. 1. The construct was then transformed into DH5α strain of *E. coli* (ATCC 53868). The colonies obtained were plated on LB medium (10 g/L tryptone, 5 g/L yeast extract, 10 g/L NaCl), with 50 µg/ml ampicillin. The plates were incubated at 37° C. degrees for 16 hours.

For secretion of the SK into the culture medium (Strategy II), the BBIL-SK vector-transformed *E. coli* was co-transformed with another vector, pJL3, which expresses Bacteriocin Release Protein (BRP) (MoBiTec GmbH, Gottingen, Germany). Induction of the BRP causes an activation of phospholipase A in the *E. coli* outer membrane. This results in the formation of permeable zones in the cell membranes, through which proteins are released into the medium. A moderate induction prevents the lysis of the host cells. An important feature of this strategy is the prevention of inclusion body formation and secretion of the formed streptokinase as an active protein into the culture medium. Another important characteristic of this strategy is the utilization of commercially available lactose as inducer.

PRODUCTION OF STREPTOKINASE

Medium composition and inoculum preparation: A single transformed colony was inoculated into 1 ml of the LB media and incubated on a shaker at 30° C. for 16–18 hours. The culture was subsequently inoculated into 10 ml of SK medium (see Table 1) in 100 ml shake flasks. Following this, two further pre-culture flasks (each 100 ml batch medium in 1000 ml shake flasks) were innoculated and incubated on a rotary shaker at 30° C. for 16–18 hours.

TABLE 1

MEDIUM FOR BATCH FERMENTATION

| Component | Grams/liter |
|---|---|
| Glucose (40%) | 70 ml |
| $(NH_4)_2 HPO_4$ | 4.0 g |

TABLE 1-continued

MEDIUM FOR BATCH FERMENTATION

| Component | Grams/liter |
|---|---|
| $KH_2PO_4$ | 13.30 g |
| Citric acid | 1.75 g |
| Trace elements | 2.500 ml |
| $CoCl_2.6H_2O$ | 1.000 g |
| $MnCl_2.4H_2O$ | 6.000 g |
| $CuSO_4.5H_2O$ | 0875 g |
| $H_3BO_3$ | 1.200 g |
| $Na_2MoO_4$ | 0.840 g |
| Zn ($CH_3C00-$) | 13.52 g |
| Fe(III) Citrate | 40.00 g |
| Vitamins (100 X) | 5 ml |
| $MgSO_4.7H_2O$ (200 X) | 10 ml |

Table 1: Represents the composition of batch fermentation for both the production of recombinant streptokinase as an inclusion body (Strategy I) as well as for secretory streptokinase (Strategy II).

Pilot scale fermentation (Strategy I—inclusion body): A 20 L B.Braun fermentor (Biostat U20G, Melsungen AG) with a working capacity of 10 L was used for both strategies. Dissolved oxygen and pH were monitored using a steam-sterilizable electrode (Ingold Wilminton, Mass.). The fermentor was inoculated with 4% inoculum.

Batch culture and controls: The initial batch culture of 10 liters was started with the following conditions:

Temperature: 30° C.
Aeration: 1.V.V.M
pH: 6.9

The dissolved oxygen was constantly maintained at 40% by increasing the speed of the stirrer. The pH was maintained by the addition of aqueous ammonia (25% w/w). The levels of glucose and acetic acid were monitored.

Figure 2:
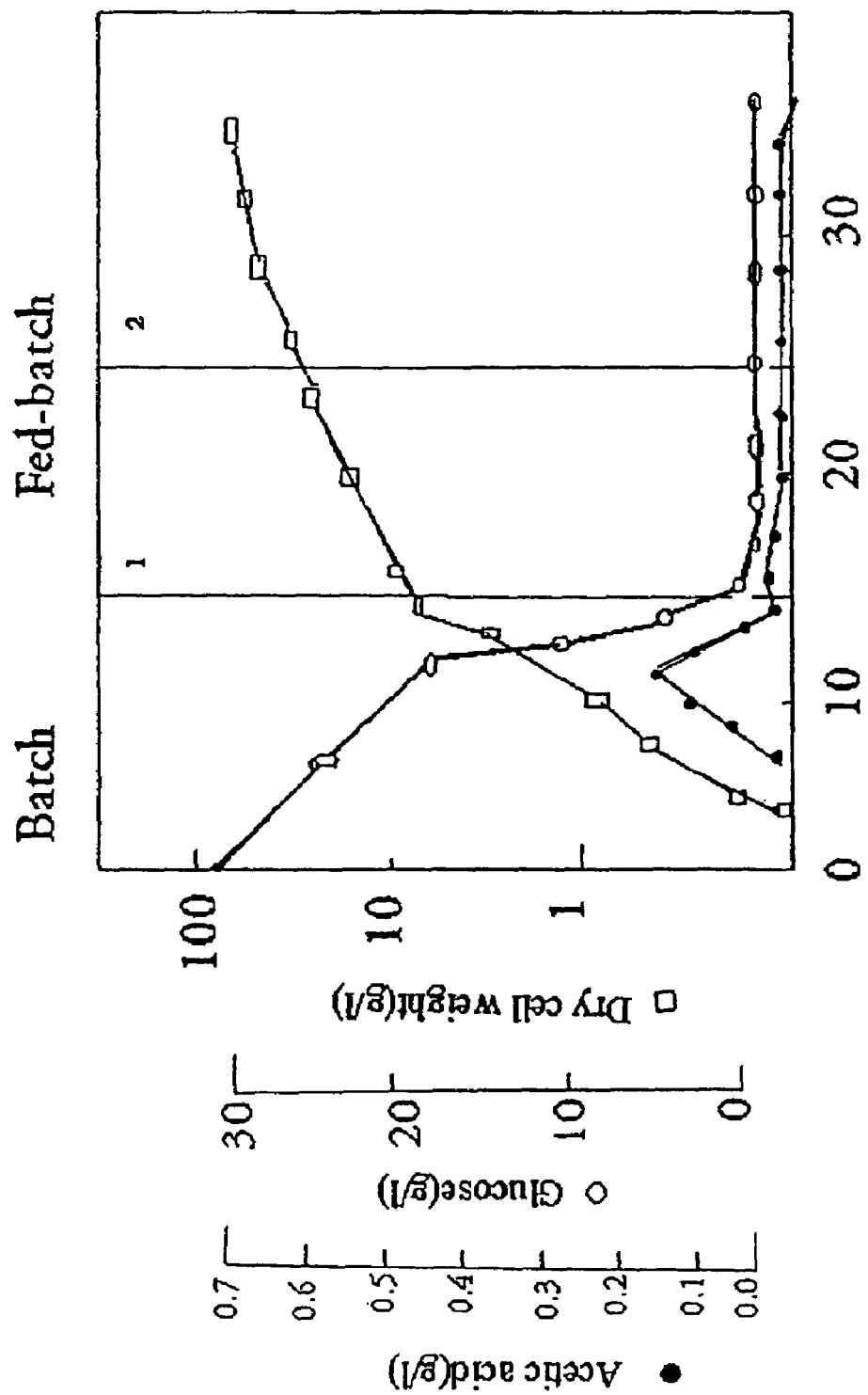
FIG. 2 is a graph showing temperature-induced production of recombinant streptokinase (as an inclusion body) showing the glucose consumption (O), dry cell weight (□), and concentration of acetic acid (●).
Figure 3:
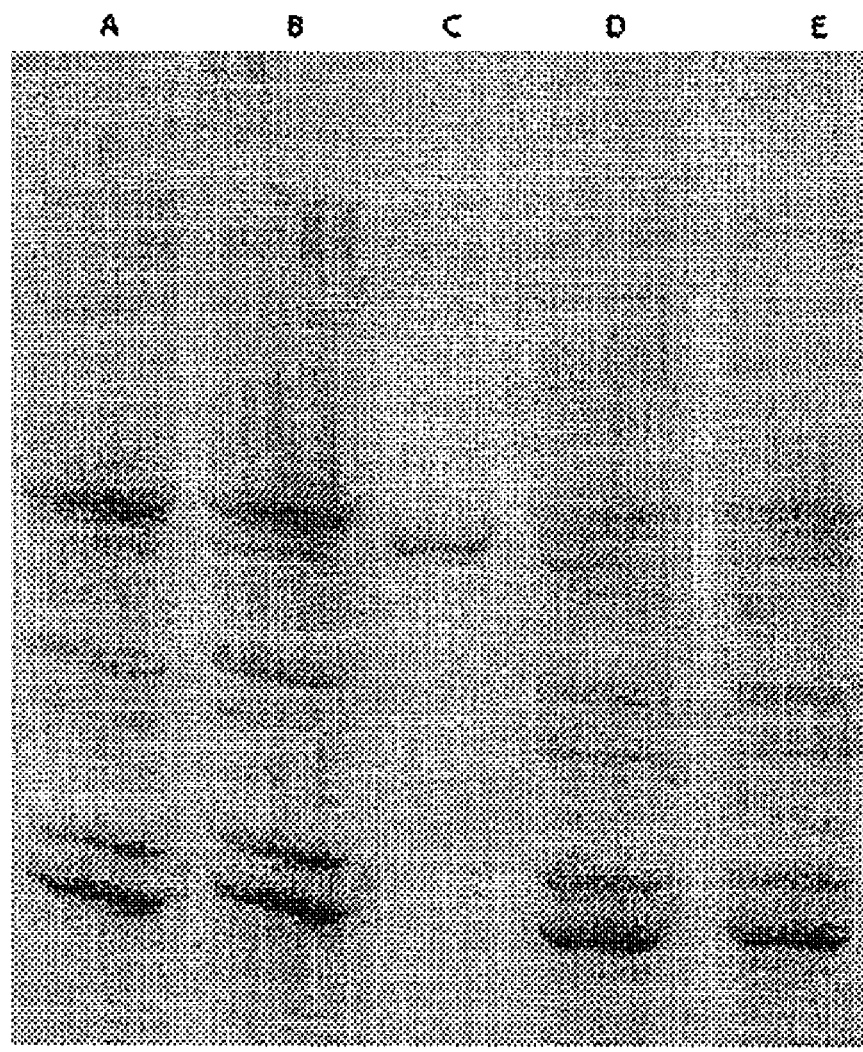
FIG. 3 is an SDS-PAGE analysis of uninduced and induced expression of streptokinase during fermentation.

Fed batch culture: Near depletion of glucose was observed after 10 hours (FIG. 2). Subsequently, the fermentation was shifted to fed batch mode wherein the substrate was added (see Table 2). All the parameters were kept constant excepting that of aeration which was increased to 2.V.V.M. These conditions were maintained for the next 15 hours. The temperature was then rapidly increased to 42° C. The increase in temperature to 42° C. caused the induction of the recombinant protein and maintaining the same for the next 4 hours attained the maximum induction (FIG. 3).

TABLE 2

MEDIUM FOR FED BATCH FERMENTATION

| Component | Volume/liter |
|---|---|
| Glucose (90%) | 407 ml |
| $MgSO_4.7H_2O$ | 170 ml |
| EDTA-Disodium | 9.0 ml |
| Trace elements | 2.5 ml |
| Vitamins | 2.5 ml |

Table 2: Represents the composition of medium for production of inclusion body (Strategy I).

Analytical methods: Cell growth was followed by measurement of the optical density at a wavelength of 600 nm (Beckmann spectrophotometer). The dry cell weight (DCW) was determined from a pellet of 1 ml culture medium. Cell pellets were resuspended in distilled water, centrifuged again and dried at 40° C. under vacuum. The levels of glucose and acetic acid were monitored by standard methods.

Figure 4:
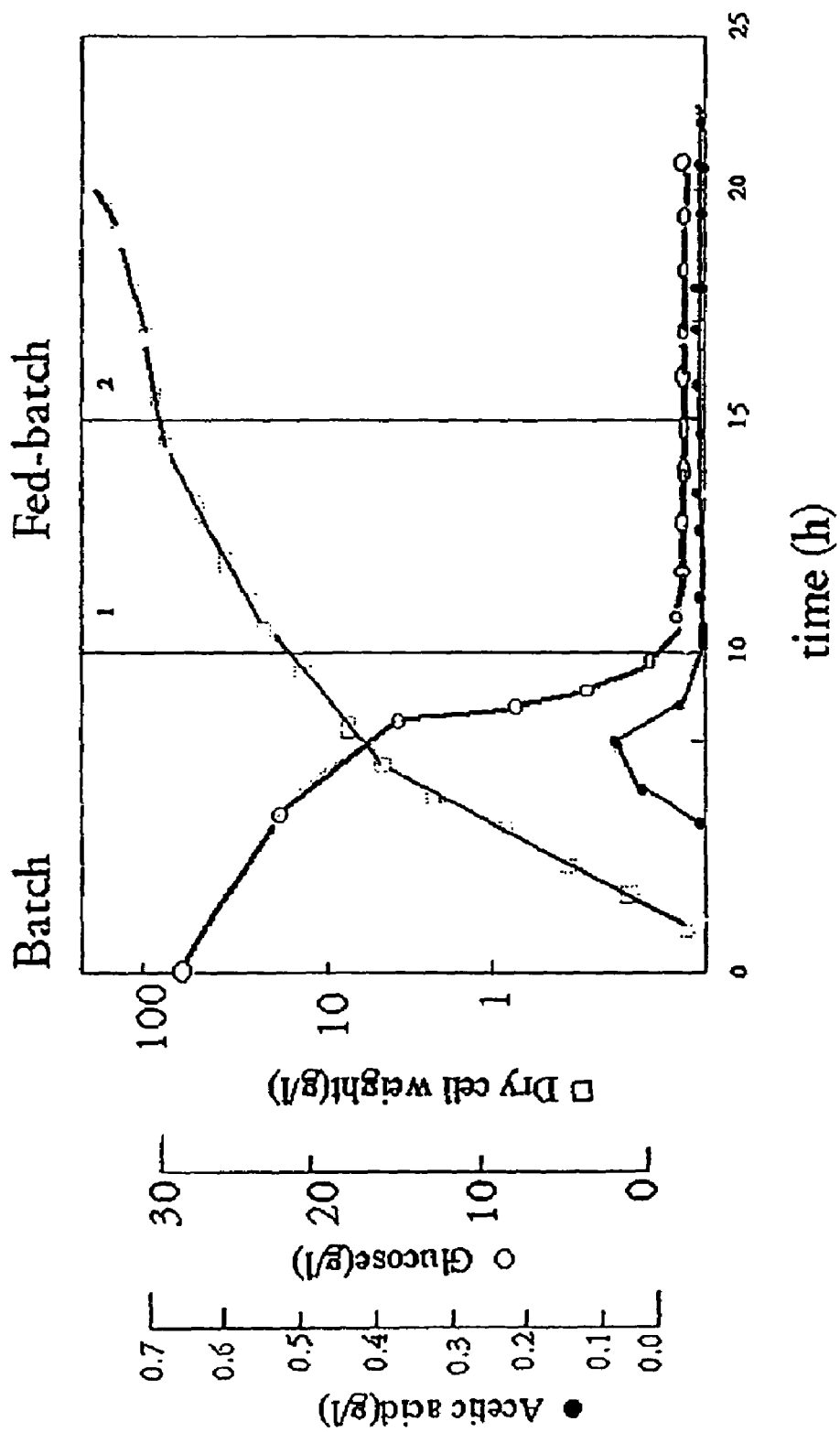
FIG. 4 is a graph showing temperature-induced production of recombinant streptokinase (secretory) showing the glucose consumption (O), dry cell weight (□), and concentration of acetic acid (●).
Figure 5:
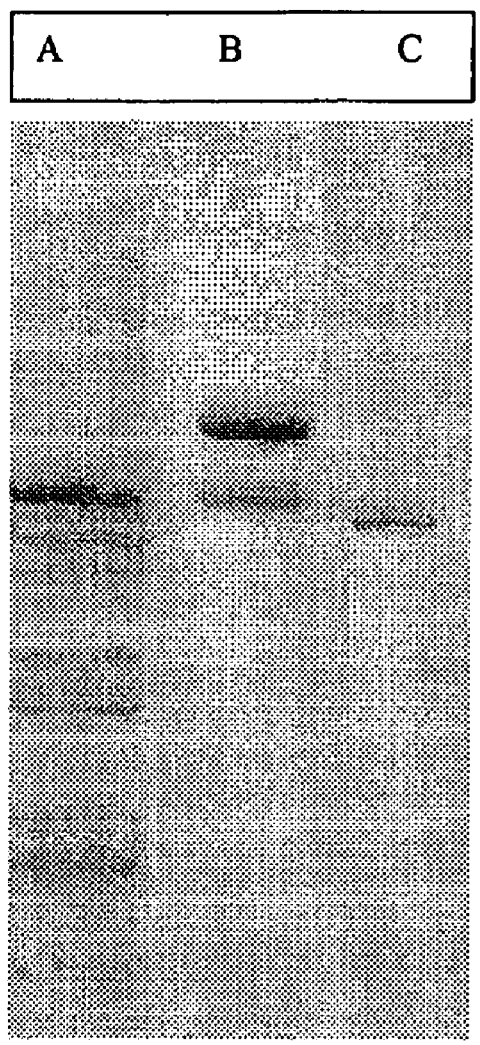
FIG. 5 is an SDS-PAGE analysis of secretory recombinant streptokinase after fermentation, purification and formulation.

Pilot scale fermentation (Strategy II): Fermentation medium components were similar to that used in Strategy I. The only addition was the use of chloromphenicol (12.5 µgms/ml). Similarly the levels of glucose and acetic acid were estimated. The fed batch fermentation was started after about 10 hours of fermentation as indicated by the near depletion of glucose (FIG. 4). The fed batch medium was composed of lactose and glucose (see Table 3). Once the glucose levels reached near depletion, a glucose fed batch was established. This was continued until the OD reached about 130, which was about 10 hours. Subsequently the induction was carried out by feeding a glucose/lactose mixture and continued for about 5 hours. The activity of streptokinase was assayed by using S-2251 substrate (H-D-Val-Leu-Lys-p-Nitroanilide). Fermentation yielded an activity of 4198 IU/mg protein (FIG. 5).

TABLE 3

MEDIUM FOR FED BATCH FERMENTATION

| Component | Volume/liter |
|---|---|
| Glucose (90%) | 407 ml |
| Lactose (30%) | 407 ml |
| $MgSO_4.7H_2O$ | 170 ml |
| EDTA-Disodium | 9.0 ml |
| Trace elements | 2.5 ml |
| Vitamins | 2.5 ml |

Table 3: Represents the composition of medium for fed batch fermentation (Secretory type-Strategy II).

PURIFICATION

Strategy I

Cell separation: The cells were centrifuged at 5000 rpm for 20 minutes using Centrikon T-124 (Kontron Instruments). The cell pellet was suspended in washing buffer containing 0.025 mM of $Na_2HPO_4$, 0.073 mM of $NaH_2PO_4$, 2.5 mM of EDTA prepared in sterile pyrogen-free water.

Cell disruption: The cells were centrifuged and further suspended in lysis buffer containing 5 mM phenyl methyl sulphonyl flouride (PMSF) with 0.5% Tween 20. The suspension was passed through a DYNO mill (Type KDL-PILOT-A, Basel, Switzerland)

Figure 6:
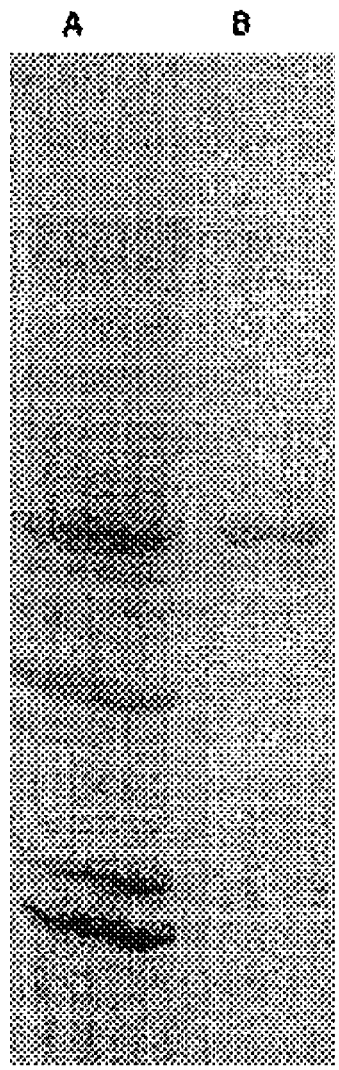
FIG. 6 is an SDS-PAGE analysis of the aqueous phase after aqueous two-phase separation and precipitation with the PEG.

Aqueous two-phase separation (ATPS): The partitioning of the inclusion body was carried out using an aqueous two-phase system containing polyethylene glycol (PEG) and NaCl. The cell suspension was treated with a quantity of NaCl needed to obtain a final concentration of 0.5 M. PEG 6000 was prepared in 25 Mm Tris-Cl, pH 8.5, and was added to the cell suspension. The suspension was stirred for 6–8 hours and was left overnight at 4° C. for the PEG precipitation. The aqueous phase containing the partially purified inclusion body was separated by centrifugation. The inclusion body was subjected to buffer exchange against 50 mM Tris-Cl, pH 8.5, using a Pellicon Ultrafilteration System (Millipore Company, Bedford, Mass., USA). The inclusion body was further purified by chromatography (FIG. 6).

Isolation of the inclusion bodies: The aqueous phase was spun at 6000 rpm/20 minute in a Centricon T124 centrifuge (Kontron Instruments). The pellet was suspended in 50 mM Tris-Cl, pH 8.0, containing 0.5% (V/V) Triton X-100, and 10 mM EDTA and incubated at room temperature for 5 minutes. This was again centrifuged as above.

Solubulization of inclusion bodies: The solubulization process was performed at room temperature. The pellet from the preceding step was suspended in Tris Buffer, pH 8.0, suspended with 8 M urea. After 2 hours, the solution was diluted with 9 volumes of 50 mM $KH_2PO_4$, pH 10.7, and left at room temperature for 2 hours. The pH was reduced to 8.0 with HCl, and the extract was left at room temperature.

Diafiltration: The urea extract was diafiltrated (Millipore 10,000 nominal molecular wt. cut off) and the final solution was concentrated to 2-folds.

Ion exchange chromatography: Purification was carried out on Bio Process Glass (BPG) column (Amersham Pharmacia, Piscataway, N.J., USA). The partially purified inclusion body was passed through DEAE-Toyapearl (Toshaas), pre-equilibrated with 50 mM Tris-Cl, pH 8.5. Elution was carried out by means of a step gradient using 200 mM and 500 mM NaCl. Elution was carried out at a flow rate of 100 ml/minute. The eluate was collected in fractions of 1 L. All of the fractions were subjected to vertical slab SDS-PAGE. Samples were run at 40 mA for about 60 minutes under denaturation conditions. The SDS profile was compared with various proteins of known standard molecular weight. The gels were stained in 0.25% R 250 Commassie brilliant blue (45:45:10: methanol: water:acetic acid) and destained (30:10:60: methanol:acetic acid:water). The inclusion body was subjected to buffer exchange against 0.05M phosphate buffer, pH 6.8, with 0.15 M NaCl through a Pellicon Ultrafilteration System (Millipore Company). The inclusion body was further purified by gel chromatography. SK activity was estimated to be 88,200 IU/mg protein.

Figure 7:
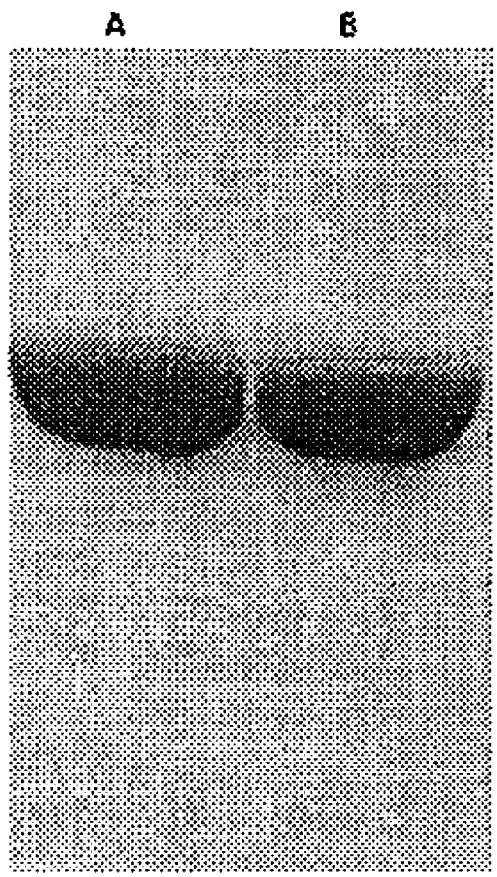
FIG. 7 is an SDS-PAGE analysis of recombinant streptokinase after ion-exchange chromatography (500 mM NaCl fraction) and gel permeation chromatography.

Gel permeation chromatography: Gel permeation was carried out on TSK Gel SW column (Tosohaas USA). The partially purifed inclusion body was passed through Sephacryl S-200 HR (Sigma). The column was equilibrated with 50 mM phosphate buffer, pH 6.8. Fractions were analyzed at 280 nm wavelength and subsequently checked for purity on SDS-gel electrophoresis as described for the ion exchange chromatography step. Streptokinase of >98% purity was obtained (FIG. 7). SK activity was estimated to be 98,500 IU/mg protein.

Diafiltration: The positive fractions were diafiltered using a Millipore filter (10,000 NMWL).

Sterilization: The purified active protein was sterilized with a 0.22 µm filter (Millipore) This was further used in the characterization, assay, formulation and lyophilization. SK activity was estimated to be 98,000 IU/mg protein.

Strategy II

After the fermentation process, the broth was clarified by passing through 0.22 µm filter (Millipore). The filtrate was treated with 5 mM PMSF and stirred for 30 minutes. This was used in the purification process.

Ion Exchange Chromatography: Purification was carried out on a Bio Process Glass (BPG) column (Amersham Pharmacia). The clarified supernatant was passed through DEAE-Toyapearl (Toshaas) pre-equilibriated with 50 mM Tris-Cl, pH 8.5. Elution was carried out by means of a step gradient using 200 mM and 500 mM NaCl. Elution was carried out at a flow rate of 100 ml/per minute. The eluate was collected in fractions of 1 Liter. All of the fractions were subjected to vertical slab SDS-PAGE. Samples were run at 40 mAmp for about 60 minutes under denaturation conditions. The SDS profile was compared with various proteins of known standard molecular weight. The gels were stained in 0.25% R 250 Commassie brilliant blue (45:45:10: methanol: water: acetic acid) and destained (30:10:60: methanol: acetic acid:water). The secretory protein was subjected to buffer exchange against 0.05M Phosphate buffer (pH 6.8) with 0.15M NaCl through a Pellicon Ultrafilteration System (Millipore Company). The partially purified secretory protein was purified by gel permeation chromatography. SK activity was estimated to be 83,500 IU/mg protein.

Gel permeation chromatography: Gel permeation was carried out on TSK Gel SW column (Tosohaas). The partially purifed inclusion body was passed through Sephacryl S-200 HR (Sigma). The column was equilibrated with 50 mM phosphate buffer (pH 6.8). Fractions were analyzed at 280 nm wavelength (Beckmann Spectrophotometer) and subsequently checked for purity on SDS-gel electrophoresis as described for the ion exchange chromatography step. SK activity was estimated to be 97,200 IU/mg protein.

Diafiltration: The positive fractions were diafiltered using a Millipore filter (10,000 NMWL).

Figure 8:
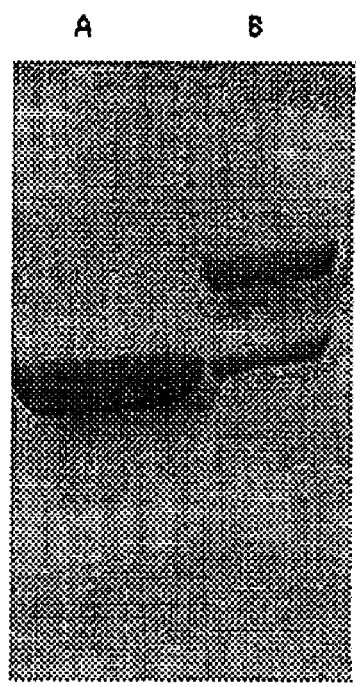
FIG. 8 is an SDS-PAGE analysis of purified streptokinase and streptokinase formulated with human serum albumin.

Sterilization: The purified active protein was sterilized with 0.22 μm filter (Millipore). SK activity was estimated to be 98,500 IU/mg protein. This was further used in the characterization, formulation and lyophilization (FIG. 8).

Characterization of Streptokinase

A. Physical Analysis

Figure 9:
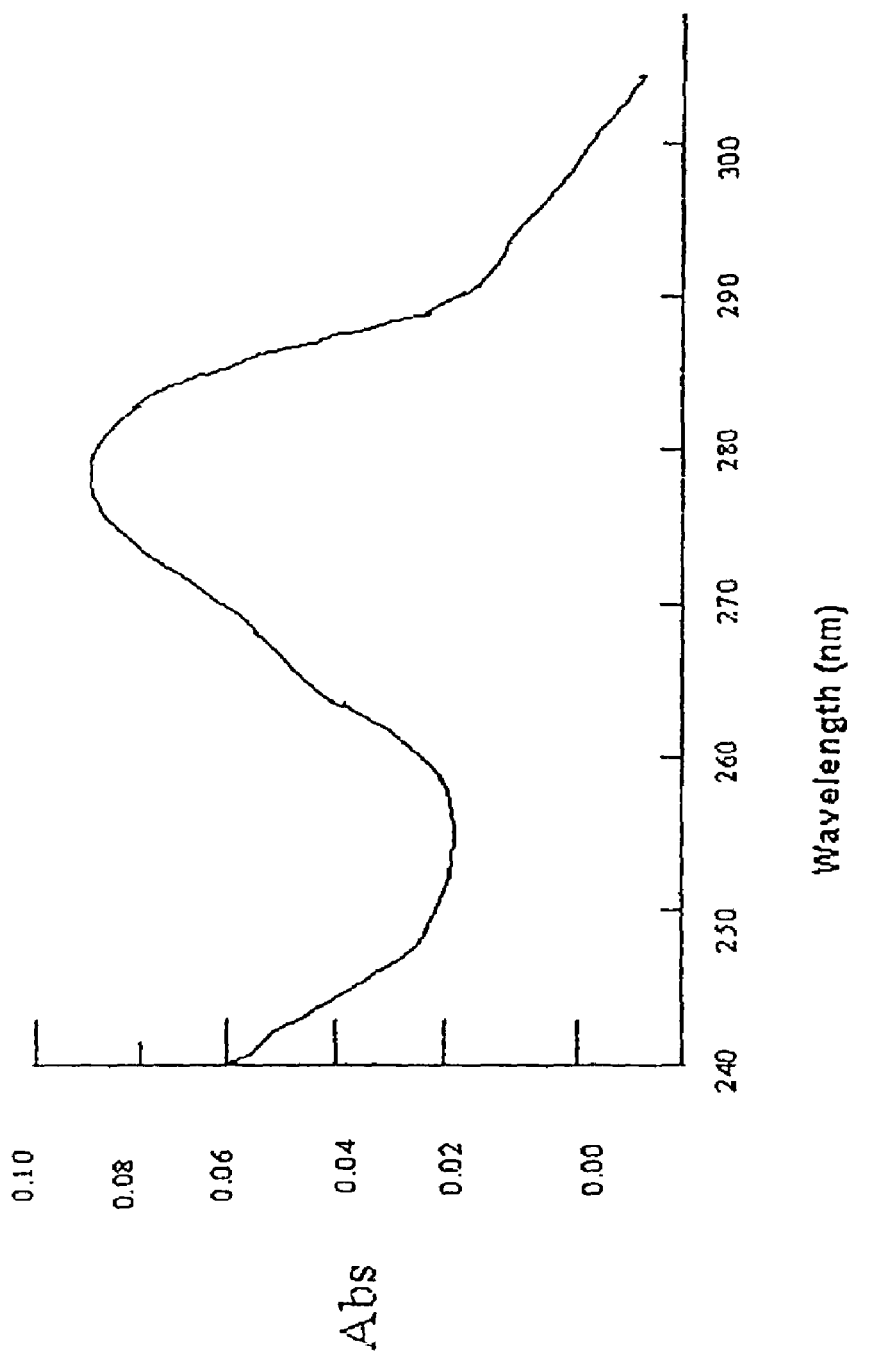
FIG. 9 is a graph showing the UV-absorption spectrum of recombinant streptokinase λ-max at 278 (nm).
Figure 10:
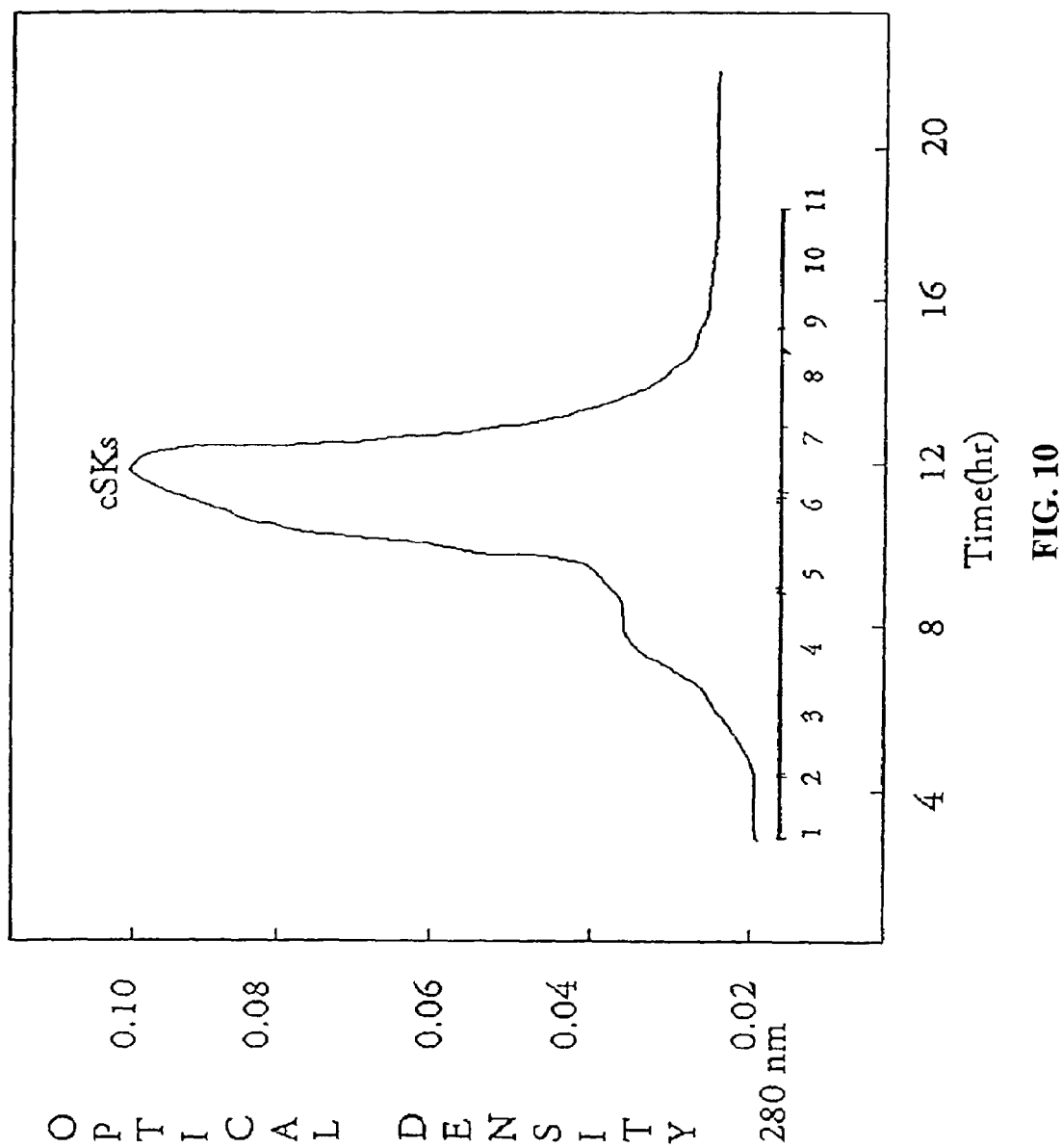
FIG. 10 is a graph showing the HPLC profile of recombinant streptokinase produced according to the present invention.
Figure 11:
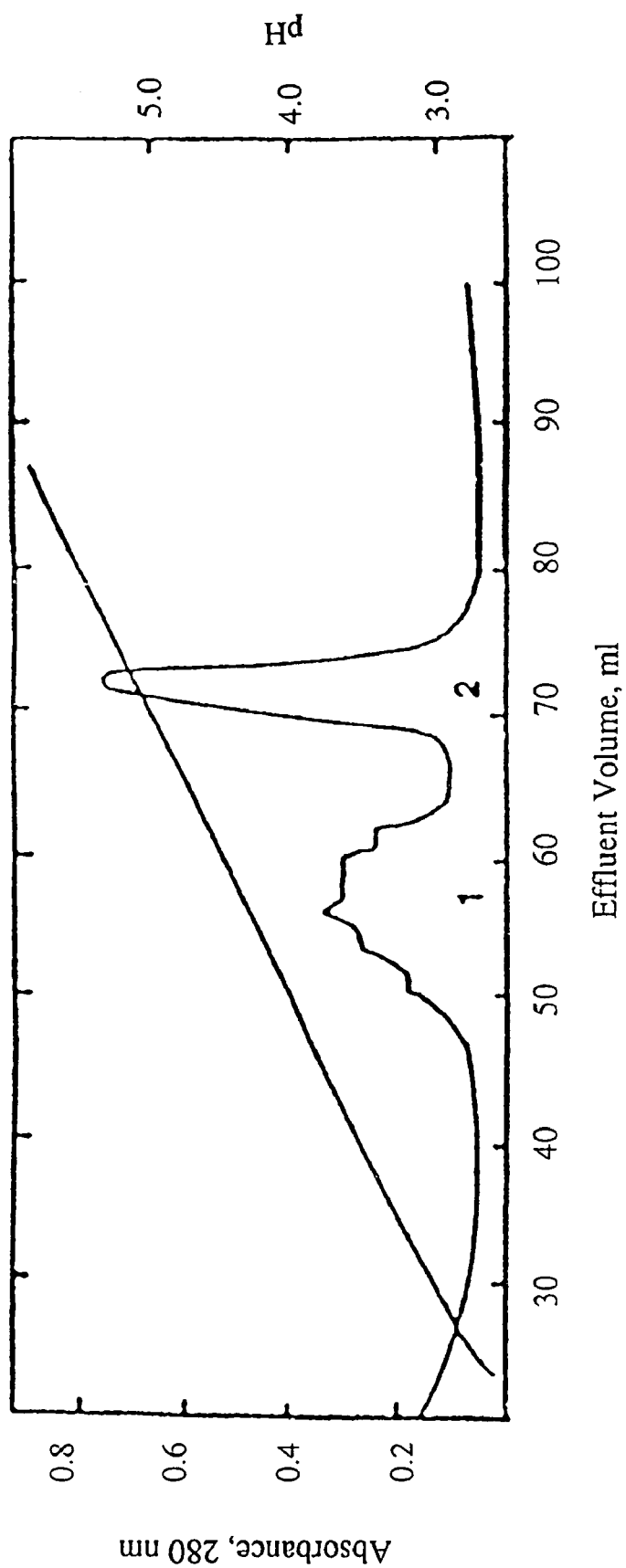
FIG. 11 is a graph showing the isoelectric focusing of recombinant streptokinase at 4° C., the absorbance at 280 nm, and a 3–6 pH gradient pH. Peak 2 contained all of the streptokinase activity.

Streptokinase is a single chain polypeptide containing no disulphide bridges due to the absence of cysteine residues. It has a molecular weight of 45,000 Dalton:
  i. UV-Spectroscopic analysis of the bulk: The UV-Spectroscopic scan of the bulk purified protein is provided. Result displayed a characteristic absorption peak at 276 nm (FIG. 9)
  ii. HPLC analysis of the bulk protein: The HPLC analysis of the bulk protein was carried out on a Kontron system 520/detector 535. A Zorbax Bioseries GF-250 gel filteration column was used for the above analysis. The analytical conditions employed were as follows:
    a) Column: Zorbax Bio series GF-250 (9.4 mm×25 cm)
    b) Guard Column: Zorbax Diol Bio series
    c) Mobile phase: 50 mM Tris-Cl, pH 7.0
    d) Flow rate: 1 ml/minute
    e) Detector: 254 nm
    f) Sample volume: 20 μl Results: Streptokinase eluted with a retention time of 7.5 minutes (FIG. 10).
  iii. Isoelectric focusing analysis (FIG. 11): Isoelectric focusing was performed on a LKB 110-ml column utilizing a temperature control system maintaining at 4° C. The sample was analysed on a gradient of pH 3–6, focused for 6–8 hours. The isoelectric point was obtained at all stages. Results: Isoelectric point equals 5.2.

B. Chemical Analysis
  i. N-Terminal amino acid sequences: N terminal analysis of the purified bulk protein was carried out using an automated Edman degradation technique. The first 12 amino acid residues were identified as follows:
    $NH_2$-ILE-ALA-GLY-PRO-GLU-TRP-LEU-LEU-ASP-ARG-PRO-SER-COOH (SEQ. ID. NO. 4)
  ii. C-Terminal amino acid sequences: The C-terminal analysis of the protein digested by Carboxipeptidase A and Carboxipeptidase Y revealed a sequence of:
    COOH-LYS-ASP-ASP-PRO-ASN-$NH_2$ (SEQ. ID. NO. 5)

Assay

A. In-Vitro Assay

A two-stage assay was used which separates the plasmin-generated reaction from the plasmin assay. In the first stage, 1 μl of streptokinase was added to 50 μl of plasminogen (200 μg/ml) in 0.05 M Tris-Cl and 0.1 M NaCl. After incubating for 15 minutes at 37° C., the resultant plasmin was assayed by the addition of 30 μl of H-Dval-Leu-Lys-p-Nitroanilide (2 mg/ml in 1 M NaCl) and further incubated for 15 minutes at 37° C. The reaction was stopped by the addition of 0.4 ml of 0.1 M NaCl in 0.5% (v/v) glacial acetic acid. The absorbance was read at 405 nm. The Second International Standard of streptokinase from "National Institute for Biological Standards and Control" was used as reference. Result: The preparation showed an activity of 97,500+/– 2500 IU/mg protein.

B) Clot Lysis Assay

Five (5) ml of fibrinogen (100 mg in 50 ml of PBS, pH 7.4), 0.2 ml of plasminogen (10 units in 1 ml of PBS, pH 7.4), and 0.2 ml of thrombin (100 units in 1 ml of PBS, pH 7.4), were mixed in a petriplate. A clot forms in about 10 minutes. A 1.0 cm diameter Whatman filter paper was placed over the clot. Different concentrations of streptokinase (control & test) were placed on the paper. Result: The dissolution of the clot was seen by the liquification of the clot. The diameter of the clearing zone was directly proportional to the activity of streptokinase.

Contamination Limits

A. Endotoxin Levels

The Limulus Amebocyte Lysate (LAL) is the most sensitive and specific means to detect and measure endotoxin, a fever-producing by-product of gram negative bacteria commonly called a pyrogen. The LAL test is generally accepted as an alternative to the rabbit pyrogen test. A commercially-available kit from Salesworth (USA) was used. Results: Repeated analysis revealed endotoxins level within limit of <0.02 units/mg protein.

B. DNA Content

The DNA content in each batch was quantified by slot blot technique. Results: DNA content of <10 pcg/1.5 million units of streptokinase was seen.

C. Carbohydrate Levels

A glucose stock solution of 0.02% was prepared and a serial dilution was made ranging from 0 to 120 μl, prepared in triplicates. Different volumes of test samples were taken and the volume was made to 200 μl. The tubes were cooled in ice for 10 minutes and 800 μl of ice-cold orcinol-sulphuric acid reagent was added. The tubes were incubated for 15 minutes at 80° C. The tubes were cooled again rapidly. The absorbance was read at 480 nm. The absorbance values of the test were read along with the controls. Results: Data revealed no carbohydrate content in the samples.

D. Lipid Levels

From a lipid standard (100 mg of cholesterol in 10 ml of chloroform), serial dilutions were made ranging from 50–200 μl. A similar range of test samples were prepared. In brief, 2 ml of $H_2SO_4$ was added to each tube and the tubes were boiled in water for 10 minutes and then cooled for 5 minutes. 0.1 ml of this mixture was pipetted into separate tubes and treated with 0.1 ml of concentrated $H_2SO_4$ and 2 ml of phosphoric acid-vanillin reagent was added. The tubes were incubated at 45° C. at room temperature and the absorbance was read at 530 nm against blank. Result: No lipid was detected in the samples. Formulation: The final bulk concentration was adjusted to about 1.5 million units/ml of phosphate buffer. Human serum albumin was added to a final volume of 120 mg and the vials were lyophilized.

Lyophilization: Lyophilization was carried out on an FTS lyophilizer. Two (2) ml of solution was taken in 5 ml vials and lyophilized by standard lyophilization procedures using an Dura Stop MP (FTS-system).

BIBLIOGRAPHY

1. Granger, C. B., Califf, R. M., Jopol, E. J. (1992), *Drugs*, 44(3):293–325.
2. Badimon, L. and Badimon, J. J. (1989), *J. Clin. Invest.*, 84:1134–1144.
3. Jorgensen, L., Rowsell, H. C., Hovig, T., Mustard, J. F. (1967). *Ann. J. Pathol*, 51:681–719.
4. Lassila, R., Badimon, J. J., Vallabhajosula, S., Badimon, L. (1990), *Arteriosclerosis*, 10:306–315.
5. Chesbro, J. H., Knatterud, G., Roberts, R., et al. (1987), *Circulation*, 76:142–154.
6. Versrate, M., Bory, M., Collen, D. et.al. (1985). *Lancet* I:842–847.
7. Topal, E. J., Califf, R. M., George, B. S. (1988). *Circulation*, 77:1100–1107.
8. Wall, T. C., Phillips, H. R., Stack, R. S. et.al. (1990). *American J. Cardiol*, 65:124–131.
9. Topal, E. J., Thrombolytic Intervention. In Topal, E. J. (Ed). Textbook of Interventional Cardiology. pp. 76–120. W.B. Saunders Co., Philadelphia, 1991.
10. Amery, A., and Claeys, H. (1970), *Hemat Rev.*, 2:233.
11. McClintock, D. K, and Bell, P. H. (1971), *Biochem. Biophys. Res. Commun*, 43:694–702.
12. Robbins, K. C., Summaria, L. (1976), *Methods in Enzymology*. 45:257–273.
13. Derenzo, E. C., Barg W. F. Jr., Boggiano, E. et al. (1963), *Biochem. Biophys Res. Commun.*, 12:105.
14. Jakson, K. W. and Tang, J. (1982), *Biochemistry*, 21:6625–6628.
15. Bernheimer, J. et al. (1942), J. Bact., 43:481–494.
16. U.S. Pat. No. 2,701,227.
17. U.S. Pat. No. 3,855,065.
18. German Democratic Republic Patent No: 249493, IPC: C12 n 15/00.
19. Malke, et.al. (1985), *Gene*, 34:357–362.
20. U.S. Pat. No. 5,296,366.
21. Sambrook, J., Fritsch, E. F., and Maniatis, T., *Molecular Cloning: A Lab Manual.* $2^{nd}$ edition. Cold Spring Harbor Laboratory Press, Cold Spring Harbor, N.Y. (1989).
22. Marson, F. A. O., Lowe, P. A., Doel, M. T. et al. (1984), *Bio/technology*, 2:800–804.
23. Radcliffe, R. and Heinze, T. (1981), *Arch. Biochem. Biophys.* 211(2):750–761.
24. Costellino, F. J., Sodetz, J. M., Brockway, W. J., Seifring, G. E. Jr. (1977), *Methods in Enzymology*, XLV:244–257.
25. Miller, G., (1959) *Anal. Chem.* 31:426–428.
26. Zoller, N and Kirsch, K. (1962) *Exp. Med.*, 135:545–550.

What is claimed is:

1. A DNA expression construct comprising, in 5' to 3' order: a λpR-λpL promoter, the promoter operationally linked to a DNA sequence encoding streptokinase, wherein the streptokinase has an amino acid sequence as encoded by the DNA sequence of SEQ. ID. NO. 3, and wherein the expression construct drives formation of inclusion bodies comprising streptokinase in a host cell transformed to contain the expression construct, and wherein the streptokinase is enzymatically active upon solubilization of the inclusion bodies.

2. The DNA expression construct according to claim 1, wherein the DNA sequence encoding streptokinase has a DNA sequence of SEQ. ID. NO. 3.

3. A method of producing streptokinase comprising transforming a host cell with an expression construct comprising, in 5' to 3' order: a λpR-λpL promoter, the promoter operationally linked to a DNA sequence encoding streptokinase, wherein the streptokinase has an amino acid sequence as encoded by DNA sequence of SEQ. ID. NO. 3, and wherein the expression construct drives formation of inclusion bodies comprising streptokinase in a host cell transformed to contain the expression construct; and then heat inducing the host cell, wherein the host cell expresses inclusion bodies comprising streptokinase, and further wherein the streptokinase is enzymatically active upon solubilization of the inclusion bodies.

4. The method of claim 3, wherein the host cell is an *E. coli* cell.

5. The method according to claim 3, further comprising: inoculating culture media with the transformed host; and fermenting the transformed host.

6. The method according to claim 5, further comprising isolating the streptokinase produced.

7. The method according to claim 6, wherein the enzymatically-active streptokinase is isolated by steps comprising:
(a) pelleting the transformed host;
(b) disrupting the transformed host to release the inclusion bodies and partitioning the released inclusion bodies;
(c) isolating the partitioned inclusion bodies;
(d) solubilizing the isolated inclusion bodies;
(e) diafiltering the solubilized inclusion bodies;
(f) purifying the diafiltered inclusion bodies by ion exchange chromatography and then by gel permeation chromatography to separate fractions containing the streptokinase; and
(g) diafiltering the fractions containing the streptokinase.

8. A genetically-engineered host cell which expresses enzymatically-active streptokinase comprising: a host cell transformed to contain an expression construct comprising, in 5' to 3' order: a λpR-λpL promoter, the promoter operationally linked to a DNA sequence encoding streptokinase, wherein the streptokinase has an amino acid sequence as encoded by the DNA sequence of SEQ. ID. NO. 3, wherein the expression construct drives formation of inclusion bodies comprising streptokinase in the host cell, and wherein the streptokinase is enzymatically active upon solubilization of the inclusion bodies.

* * * * *